(12) United States Patent
Mohajeri

(10) Patent No.: US 8,652,993 B2
(45) Date of Patent: Feb. 18, 2014

(54) DOPED PALLADIUM CONTAINING OXIDATION CATALYSTS

(75) Inventor: Nahid Mohajeri, Rockledge, FL (US)

(73) Assignee: University of Central Florida Research Foundation, Inc., Orlando, FL (US)

(*) Notice: Subject to any disclaimer, the term of this patent is extended or adjusted under 35 U.S.C. 154(b) by 0 days.

(21) Appl. No.: 13/588,779

(22) Filed: Aug. 17, 2012

(65) Prior Publication Data

US 2013/0045858 A1 Feb. 21, 2013

Related U.S. Application Data

(60) Provisional application No. 61/524,937, filed on Aug. 18, 2011.

(51) Int. Cl.
*B01J 23/32* (2006.01)

(52) U.S. Cl.
USPC .......................... 502/325; 502/300; 502/100

(58) Field of Classification Search
USPC ............ 73/31.5, 31.7; 422/92, 428; 436/144; 442/404, 428
See application file for complete search history.

(56) References Cited

U.S. PATENT DOCUMENTS

| | | | |
|---|---|---|---|
| 3,935,157 A * | 1/1976 | Schiller et al. ................. | 523/200 |
| 5,849,073 A * | 12/1998 | Sakamoto et al. ............. | 106/437 |
| 7,446,939 B2 * | 11/2008 | Sharma et al. ................. | 359/599 |
| 2006/0216496 A2 * | 9/2006 | Gray et al. ..................... | 428/323 |
| 2007/0224081 A1 | 9/2007 | Bokerman et al. | |

* cited by examiner

*Primary Examiner* — Colleen Dunn
*Assistant Examiner* — Haytham Soliman
(74) *Attorney, Agent, or Firm* — Jetter & Associates, P.A.

(57) ABSTRACT

A supported oxidation catalyst includes a support having a metal oxide or metal salt, and mixed metal particles thereon. The mixed metal particles include first particles including a palladium compound, and second particles including a precious metal group (PMG) metal or PMG metal compound, wherein the PMG metal is not palladium. The oxidation catalyst may also be used as a gas sensor.

14 Claims, 3 Drawing Sheets

DOPED PALLADIUM CONTAINING OXIDATION CATALYSTS

CROSS REFERENCE TO RELATED APPLICATIONS

This application claims the benefit of Provisional Application Ser. No. 61/524,937 entitled "DOPED PALLADIUM CONTAINING OXIDATION CATALYSTS", filed Aug. 18, 2011, which is herein incorporated by reference in its entirety.

U.S. GOVERNMENT RIGHTS

This invention was made with U.S. Government support under Florida Hydrogen Initiative contract #DEFC3604GO14225 awarded by the U.S. Department of Energy. The Government has certain rights in the invention.

FIELD

Disclosed embodiments relate to palladium containing catalysts or gas sensors.

BACKGROUND

One of the future alternatives to current fossil-based transportation fuels has been centered on hydrogen gas ($H_2$). Currently, $H_2$ is the primary energy source of today's space exploration projects (e.g., as rocket propellant). It is also used in fuel cells that power a variety of machinery including automobiles. Furthermore, $H_2$ is an important industrial commodity produced and used in many industries. For example, it is used for the reduction of metal oxides (e.g. iron ore), ammonia synthesis, and production of hydrochloric acid, methanol and higher alcohols, aldehydes, hydrogenation of various petroleum, coal, oil shale and edible oils, among others. However, $H_2$ is a colorless, odorless gas, and is also a flammable gas with a lower explosive limit of about 4% in air. Therefore reliable $H_2$ sensors are required to detect $H_2$ leaks wherever $H_2$ is produced, stored, or used.

To detect $H_2$, sensors comprising a palladium alloy Schottky diode formed on a silicon substrate are known. These sensors are based on metal-oxide-semiconductor (MOS) technology that is used in the semiconductor industry. The gas sensing MOS structures comprise a $H_2$-sensitive metal (palladium or its alloy) on a dielectric (e.g., an oxide) adherent to a semiconductor. This $H_2$ sensor has been commercialized and exploited for detecting $H_2$ leaks during pre-launches of space vehicles. Others have also used palladium or the like as a sensing element for detecting $H_2$. A $H_2$ sensor containing an array of micromachined cantilever beams coated with palladium/nickel has also been disclosed.

Semiconductors with wide band-gap (e.g. gallium nitride) have also been used to make diodes for $H_2$ detection. One of the concerns for all of these types of sensors using palladium or the like is the requirement of a high operating temperature (greater than 200° C.) and further elevated temperatures (greater than 500° C.) to reactivate the sensing element, bringing about lengthy analysis. Another issue is sensitivity of the sensing element to unintended compounds that are commonly found in the atmosphere, including water vapor, various hydrocarbons, and various reducing gases such as carbon monoxide and hydrogen sulfide. Although not conventionally used, chemochromic $H_2$ sensors are known. Some chemochromic $H_2$ sensors lack field stability and have a tendency to crack and peel and some can be washed off by precipitation and/or condensation. Moreover, some chemochromic $H_2$ sensors do not show selectivity to $H_2$.

Thus, there remains a need for an improved, reliable and durable chemochromic $H_2$ sensor, or more generally an oxidation catalyst for a chemochromic reducing gas sensor or catalyst, for a variety of applications, including space, transportation, oil refineries, and chemical plants.

SUMMARY

This Summary is provided to introduce a brief selection of disclosed concepts in a simplified form that are further described below in the Detailed Description including the drawings provided. This Summary is not intended to limit the claimed subject matter's scope.

A supported oxidation catalyst comprises a support including a metal oxide or metal salt, and metal particles are on the support. As used herein, a "support" refers to a material in which the metal particles are deposited onto in the formation of the supported oxidation catalyst. The support can be in layer form on another layer, such as a layer comprising a plurality of bound particles on a solid surface, or be in discrete particle form. The metal particles generally comprise mixed metal particles which refers to herein as including at least two different metal particles compositions including a palladium compound (e.g., PdO). However, in the embodiment the support comprises barium sulfate, the metal particles can comprise only a single metal composition, such as PdO.

When the metal particles comprise mixed metal particles, the mixed metal particles include first particles comprising a palladium compound (e.g., PdO) and second particles comprising a precious metal group (PMG) metal or PMG metal compound, wherein the PMG metal is not palladium. The PMG metal can comprise gold, silver or one of the platinum group metals other than palladium, including platinum.

Disclosed supported oxidation catalysts can be used as a pigment for hydrogen sensing/detection or other sensing/detection of other reducing gases where they may be encapsulated in a reducing gas permeable polymer matrix such as silicone rubber or silicone resin. In another embodiment, the supported oxidation catalyst is used as a catalyst without polymer encapsulation.

DETAILED DESCRIPTION

Figure 1A:
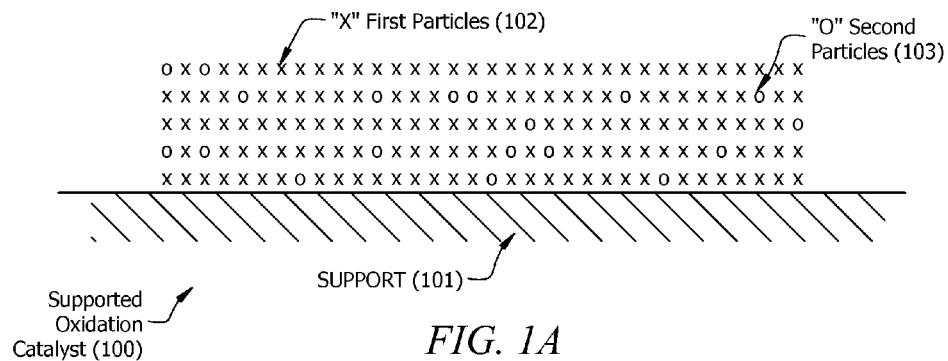
FIG. 1A is a cross sectional depiction of an example supported oxidation catalyst comprising a support, and mixed metal comprising particles on the support including first particles comprising a palladium compound and second particles comprising a precious metal group (PMG) metal or PMG metal compound, where the PMG is not palladium, according to an example embodiment.
Figure 1B:
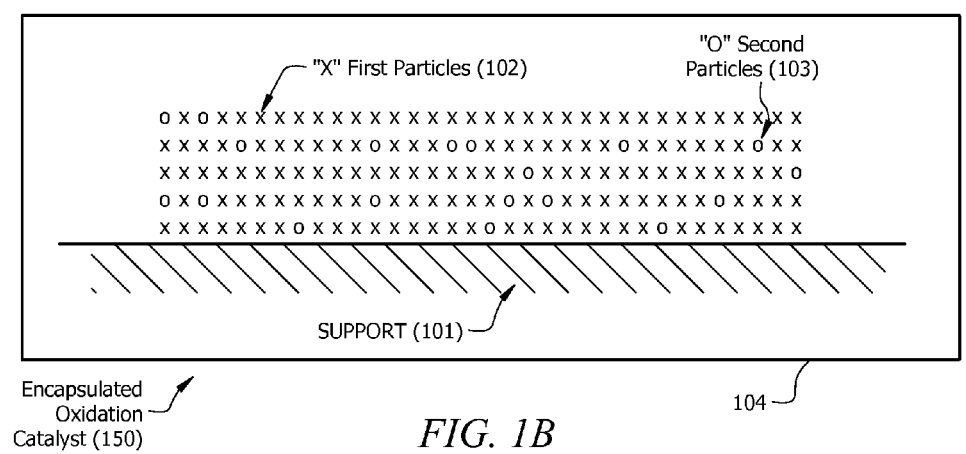
FIG. 1B is a cross sectional depiction of an example encapsulated supported oxidation catalyst comprising the oxidation catalyst in FIG. 1A along with an optional reducing gas permeable polymer that forms a continuous phase which provides complete encapsulation for the support and metal comprising particles, according to an example embodiment.

Disclosed embodiments in this Disclosure are described with reference to the attached figures, wherein like reference numerals are used throughout the figures to designate similar or equivalent elements. FIGS. 1A and 1B are not drawn to scale, and they are provided merely for illustration. Several aspects are described below with reference to example applications for illustration.

It should be understood that numerous specific details, relationships, and methods are set forth to provide a full understanding of the disclosed embodiments. One having ordinary skill in the relevant art, however, will readily recognize that the subject matter disclosed herein can be practiced without one or more of the specific details or with other methods. In other instances, well-known structures or operations are not shown in detail to avoid obscuring structures or operations that are not well-known. This Disclosure is not limited by the illustrated ordering of acts or events, as some acts may occur in different orders and/or concurrently with other acts or events. Furthermore, not all illustrated acts or events are required to implement a methodology in accordance with this Disclosure.

Notwithstanding that the numerical ranges and parameters setting forth the broad scope of this Disclosure are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5.

Some disclosed embodiments are based on the discovery that a palladium compound oxidation catalyst such as PdO on a support when "doped" with particles comprising a PMG metal or PMG metal compound where the PMG metal is not palladium, provides supported oxidation catalysts which oxidize a reducing gas (e.g., hydrogen, carbon monoxide, or hydrocarbons) with oxidation kinetics sped up significantly and sensitivity increased significantly as compared to the palladium compound (PdO) on the support oxidation catalyst alone. Other disclosed embodiments are based on the discovery that the support selection of a material other than titania such as $BaSO_4$ also improves oxidation kinetics and detection sensitivity. These embodiments may be combined, by combining doping of the palladium compound (e.g., PdO) with a PMG metal or PMG metal compound and $BaSO_4$ supports, which may further improve oxidation kinetics and detection sensitivity.

The support is generally selected so that interaction of the metal particles with the surface of support surfaces minimizing the total energy required for palladium compound (e.g., PdO) reduction. This suggests a small chemical interaction between support and the metal particles and hence destabilization of the palladium compound particles on the surface of the support. For PdO on a $TiO_2$ support surface, the second PMG metal "dopant" (e.g. Pt) lowers the activation energy required for PdO reduction.

Disclosed supported oxidation catalysts embodied as chemochromic sensors (pigments) change color in a presence of at least one reducing gas. Embodied as chemochromic reducing gas sensors, disclosed reducing gas sensors are irreversible sensors. Disclosed PMG's can utilize the PMG metals of gold, silver, or platinum group metals, such as ruthenium, rhodium, osmium, iridium, and platinum.

The response time of disclosed chemochromic reducing gas sensors toward H2 gas by including nanosized PMG dopant particles, wherein the PMG is not palladium, with palladium compound particles (e.g., PdO) has been found to unexpectedly be decreased by about 10 fold while encapsulated in a silicone resin. As noted above, disclosed supported oxidation catalysts can also be used as catalysts, such as to reduce undesirable emissions from fossil fuel powered vehicles.

FIG. 1A is a cross sectional depiction of an example supported oxidation catalyst 100 comprising a support 101 that can comprise a plurality of metal oxide or metal salt (e.g. sulfate) particles, first particles 102 comprising palladium compound (e.g., PdO), and second particles 103 comprising a PMG metal or PMG metal compound wherein the PMG is not palladium, on the support 101, according to an example embodiment. In typical applications, the supported oxidation catalyst 100 can be adhered to a substrate where it can provide its chemochromic reducing gas sensing or catalyst function, such as on a metal surface (e.g. a metal wall). The shapes of the support 101, first particles 102 and second particles 103 shown in FIG. 1A are arbitrary.

As noted above, although the support 101 is shown in FIG. 1A in layer form, such as comprising a polycrystalline layer, support 101 may also be in discrete particle form. Typically the support 101 comprises metal oxide or metal salt particles, mixed metal oxide particles, but can also comprise their salts. For pigment (chemochromic) applications, the support 101 comprises particles which are generally colorless, white, or slightly colored. The metal oxide particles can comprise transition metal oxide particles and the metal salt particles can comprise alkaline earth salt particles.

The transition metal oxide particles can comprise Group IV metal oxide particles, such as such $ZrO_2$, $SrTiO_3$, $AlTiO_3$ or $SrZrO_3$. The metal salt particles can comprise alkaline earth metal salt particles, such as $BaSO_4$. The support can also comprise titanium (e.g., embodied as $TiO_2$), and cerium (e.g., embodied as $CeO_2$). In one embodiment, the support 101 comprises particles having a size in a range from 0.1 μm to 1.0 μm, and in one particular embodiment from 0.2 μm to 0.25 μm for pigment applications to maximize opacity.

The first particles 102 can comprise palladium oxide, palladium hydroxide, or a palladium salt. The first particles 102 can have a median size in the range of 2 nm to 8 nm. The second particles 103 can comprise gold, silver, or a PGM metal other than palladium, such as ruthenium, rhodium, osmium, iridium, or platinum, or a PMG metal compound comprising PMG metal oxides, hydroxides, or hydrated oxides. In certain embodiments the PMG metal compounds can comprise PMG salts (e.g., tetra or hexachlorometalates, acetates, or other carboxylates such as propionates), or PGM metal complexes such as acetylacetonates, dichlorodiammine, and tetraammine. In one embodiment the second particles 103 have a median size in the range from 5 nm to 10 nm. The relative concentration ratio of the second particle 103 to first particle 102 ranges from 1:10 to 1:25 by weight.

The supported oxidation catalyst 100 can further comprise an ultraviolet (UV) absorber or UV Blocker, or a mixture thereof to remedy possible adverse environmental effects. The UV blocker can comprise $ZnO_2$ or $TiO_2$. The UV absorber can comprises compounds from the triazine family, such as benzotriazol or a benzopheneone. The UV absorber or UV Blocker can be in the range of 1-10 wt. % of the supported oxidation catalyst 100. Although not shown in FIG. 1A, UV absorber or UV Blocker particles if shown would be on the support 101 analogous to first particles 102 or second particles 103, or be physically mixed with supported oxidation catalyst 100.

FIG. 1B is a depiction of an example encapsulated supported oxidation catalyst 150 that comprises the supported oxidation catalyst 100 shown in FIG. 1A along with an optional reducing gas permeable polymer 104 that forms a continuous phase (matrix) which provides complete encapsulation for the support 101, first particles 102, and second particles 103, according to an example embodiment. The gas permeable polymer 104 continuous phase can be formed by admixing a suitable material, such as a moisture curable or heat curable silicone sealant with dry catalyst particles or its slurry comprising support particles 101, first particles (palladium compound) 102, and second particles (PMG metal or PMG metal compound, not palladium) 103 in a liquid phase before drying, and then curing the silicone sealant to form a rubbery gas permeable silicone polymer that forms a continuous phase that provides complete encapsulation.

In some embodiments, the supported oxidation catalyst can comprise a composite layer. A composite layer is known in the material arts and is defined herein as a composite engineered material made from two or more constituent materials with significantly different physical or chemical properties which remain separate and distinct on a macroscopic level within the finished structure. In principle, composites can be constructed of any combination of two or more materials, metallic, organic, or inorganic; but the constituent forms are typically more restricted. The matrix provided by the gas permeable polymer 104 is the body constituent, acting as a continuous phase having the other materials referred to as the additive phases embedded therein, with the gas permeable polymer 104 serving to enclose the other composite components and give it bulk form.

Disclosed embodiments also include methods of forming disclosed doped supported oxidation catalysts. A support is provided, such as comprising a plurality of metal oxide or metal salt particles. A palladium compound (e.g., PdO) and a PMG metal or PMG metal compound other than Pd are deposited on the support(s) in a liquid phase slurry including a solvent to form nanosized palladium compound (e.g., PdO) particles and PMG metal or PMG metal compound particles other than Pd particles. A solid-liquid separation process such as filtering the slurry allows removal of the liquid phase to form dried solid supported oxidation catalyst which may be referred to as composite particles.

The depositing can comprise co-depositing the palladium compound and PMG metal or PMG metal compound using a precursor for the palladium compound and a precursor for the PMG metal or PMG metal compound. As described below, depositing the palladium compound after depositing the PMG metal, PMG metal compound may provide enhanced sensing performance.

In one embodiment, the method further comprises admixing a moisture curable silicone sealant with the particles in the liquid phase, and then curing the moisture curable silicone sealant to form a rubbery gas permeable silicone polymer. In this embodiment, the gas permeable polymer provides a continuous phase that completely encapsulates the palladium compound, the PMG metal, PMG metal compound, and the supports.

As noted above, disclosed supported oxidation catalysts can be used in a variety of applications including in the development of chemochromic passive sensors for detecting reducing gases such as hydrogen, carbon monoxide, and hydrocarbons (e.g., natural gas or propane). These gases/liquids are widely used and produced in many industries and a safe operation is a top priority for all of them. Disclosed supported oxidation catalysts can also provide a layer of protection against accidental releases of these gases and therefore reinforces a safe manufacturing/utilization environment. Furthermore, disclosed supported oxidation catalysts can be used as catalysts in the automotive industry to reduce hydrocarbon, carbon monoxide, and NOx emissions, or in any industry that carry methane combustion such as natural gas-powered vehicles. Other example applications include depollution of natural gas-powered vehicles, and catalytic processes for energy production from natural gas.

The effectiveness of gas sensors, such as disclosed supported oxidation catalysts used as chemochromic reducing gas sensors, is typically evaluated by measuring the time necessary to reach a given level of color change, and by determining the total amount of color change. The latter is expressed as ΔE and is measured by a colorimeter. ΔE measures a difference in color by measuring specific parameters of the film (L, a, b). These parameters refer to a color system for measuring absolute chromaticity, L*a*b* and color difference Δ(L*a*b*) or ΔE. Color is defined in three dimensions: hue, chroma (saturation) and lightness. L*=the gradient from light to dark, a*=the gradient from red to green, and b*=the gradient from yellow to blue, and $\Delta E^* = \{(\Delta L^*)^2 + (\Delta a^*)^2 + (\Delta b^*)^2\}^{1/2}$. This equation gives a standard measurement technique by which one can compare color changes from different chemochromic reducing gas sensor film samples. The greater the ΔE* value, the greater the color contrast. Chemochromic reducing gas sensor films can be analyzed both before and after exposure to the reducing gas, allowing quantification of the intensity of the color change.

EXAMPLES

Disclosed embodiments are further illustrated by the following specific Examples, which should not be construed as limiting the scope or content of this Disclosure in any way.

For example, although Pt is generally used as the "dopant" in these examples, Pt can be replaced by gold, silver, or a platinum group metal other than platinum. Example methods of preparation of disclosed supported oxidation catalysts are now described. Samples referred to as "base" in FIGS. 2-5 such as PK-1-135 NM1 described below refer to known PdO on $TiO_2$ controls (no Pt doping). For testing, the samples were all placed inside a vial and were exposed to 100% $H_2$ gas with a 45 ml/min flow rate.

Example 1

Depositing 0.3 Wt. % Pt Doping onto PdO/TiO$_2$ by Reflux

Example 1-A

To deposit PdO particles on TiO$_2$ (titania), a slurry of 2.5 g TiO$_2$ in 100 mL water was adjusted to pH 10.6 using 12 M NaOH and stirred at 70° C. for an hour. 2.5 mL of 0.281M PdCl$_2$ solution in 2 M HCl was added dropwise to the mixture, taking care to keep the solution at pH 10.6 using 12 M NaOH. Once all the PdCl$_2$ solution was added, the pH of the mixture was adjusted to 8 using 3 M HCl. This mixture was stirred and heated for an hour while the PdO was deposited onto the surfaces of the titania. The resulting PdO/TiO$_2$ solid product was then filtered, washed thoroughly with water, and dried under vacuum at 200° C. for 3 hours. The PdO/TiO$_2$ solid product was used to provide the PK-1-135 NM1 controls.

Example 1-B 0.019 g Na$_2$PtCl$_6$ was added to a slurry of 2.5 g PdO/TiO$_2$ in 100 mL DI water. 0.027 g sodium citrate was added to the mixture, which was then placed under reflux at 70° C. and stirred overnight (~16 hours). The Pt on PdO/TiO$_2$ solid product was filtered, washed thoroughly with water and dried under vacuum at room temperature to provide a disclosed supported oxidation catalysts identified as PK-1-136-NM13.

Figure 2:
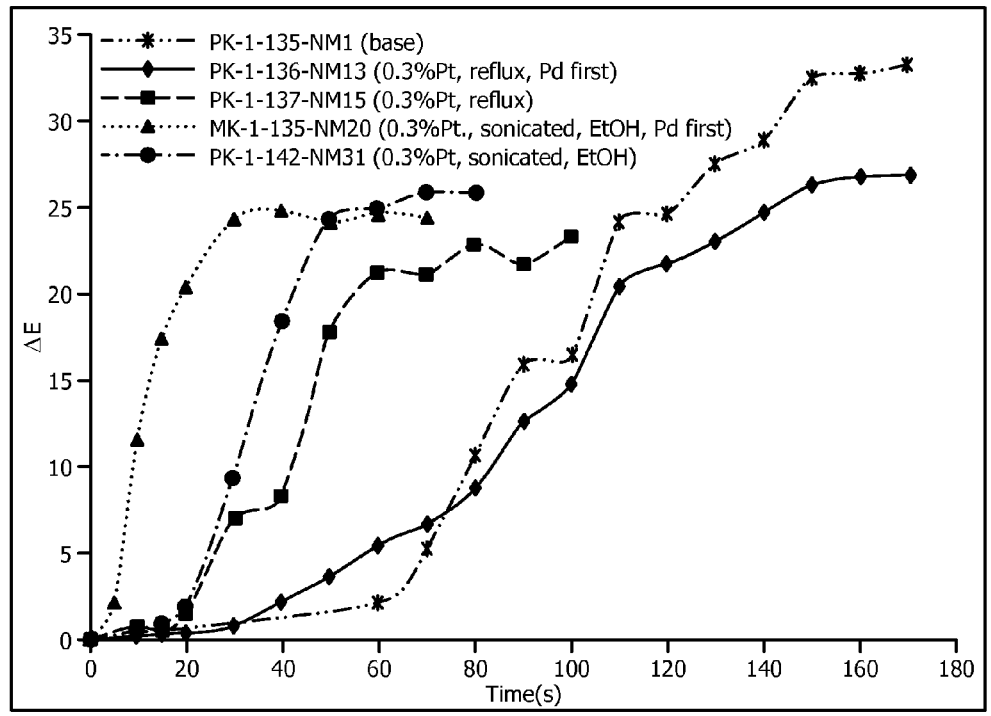
FIG. 2 shows ΔE vs. exposure time to 100% $H_2$ gas sensing performance for various disclosed platinum-doped Pd/$TiO_2$ supported oxidation catalysts used as pigments encapsulated in DOW 734® silicone resin that were synthesized as compared to a known PdO on $TiO_2$ control (no Pt doping).

FIG. 2 which shows ΔE vs. exposure time to 100% H$_2$ gas for various disclosed Pt doped PdO/TiO$_2$ supported oxidation catalysts used as pigments encapsulated in DOW 734® silicone resin, along with PK-1-135 NM1 ("Base") for a PdO on TiO$_2$ control. The performance of PK-1-136-NM13 can be seen to be similar to PK-1-135 NM1.

PK-1-137-NM15 was prepared by reversing the order of steps 1-A and 1-B. First Pt was deposited onto a TiO$_2$ support (Step 1-B) and then PdO was deposited onto Pt/TiO$_2$ by following step 1-A (its ΔE vs. exposure time to 100% H$_2$ gas is shown in FIG. 2). PK-1-137-NM15 can be seen to provide a significant performance enhancement compared to the PK-1-135 NM1 "base" control and PK-1-136-NM13.

Example 2

Depositing 0.3 Wt % Pt onto a PdO/TiO$_2$ Support by Sonication

Example 2-A

To deposit PdO, a slurry of 2.5 g TiO$_2$ in 100 mL water was adjusted to pH 10.6 using 12 M NaOH and stirred at 70° C. for an hour. 2.5 mL of 0.281M PdCl$_2$ solution in 2 M HCl was added dropwise to the mixture, taking care to keep the solution at pH 10.6 using 12 M NaOH. Once all the PdCl$_2$ solution was added, the pH of the mixture was adjusted to 8 using 3 M HCl. This mixture was stirred and heated for an hour while the PdO was deposited onto the surfaces of the titania. The solid PdO/TiO$_2$ product was filtered, washed thoroughly with water and dried at room temperature.

Example 2-B

Then, 0.019 g Na$_2$PtCl$_6$ was added to a slurry of 2.5 g PdO/TiO$_2$ in 100 mL ethanol to give a loading of 0.3 wt % Pt on the support. The pH of the solution was adjusted to 6 using 12 M NaOH. Sonication was carried out on the reaction mixture using a direct immersion titanium tip (20 kHz, 100 W cm$^{-2}$) at room temperature. The solid Pt on PdO/TiO$_2$ product was filtered, thoroughly washed with ethanol, and dried at room temperature and baked at 200° C. for 3 hrs to provide PK-1-135-NM-20 (its ΔE vs. exposure time to 100% H$_2$ gas is shown in FIG. 2). PK-1-135-NM-20 can be seen to provide a significant performance enhancement compared to the PK-1-135 NM1 "base" control.

PK-1-142-NM31 was prepared by reversing the order of steps 2-A and 2-B. First, Pt was deposited onto a TiO$_2$ support (Step 2-B), and then PdO was deposited onto Pt/TiO$_2$ by following step 2-A (its ΔE vs. exposure time to 100% H$_2$ gas is shown in FIG. 2). PK-1-142-NM31 can also be seen to provide a significant performance enhancement compared to the PK-1-135 NM1 "base" control.

Example 3

Synthesis of Irreversible BaSO$_4$/PdO 3 wt % PdO Chemochromic Pigment (BaSO$_4$ Supports)

A slurry of 2.5 g BaSO$_4$ in 100 mL water was adjusted to pH 10.6 using 12 M NaOH and stirred at 70 C for an hour. 2.5 mL of 0.281M PdCl$_2$ solution in 2 M HCl was added dropwise to the mixture, taking care to keep the solution at pH 10.6 using 12 M NaOH. Once all the PdCl$_2$ solution was added, the pH of the mixture was adjusted to 7 using 3 M HCl. This mixture was stirred and heated for an hour while the PdO was deposited onto the surfaces of the BaSO$_4$. The solid product was filtered, washed thoroughly with water and dried under vacuum at 110 C for 3 hours to provide PK-2-124-NM48C-1 (shown in FIG. 5). The catalyst PK-2-142-NM55 (shown in FIG. 5) was synthesized by adding ethanol to PK-1-124-NM48C-1 and sonicating the slurry using a direct immersion titanium tip (20 kHz, 100 W cm$^{-2}$) at room temperature. PK-2-142-NM55 can be seen in FIG. 5 to provide a significant performance enhancement compared to the PK-2-50 NM1-1 "base" control.

Example 4

Exposure of Pt-Doped PdO/TiO$_2$ Pigments to 100% Hydrogen Gas

A series of disclosed platinum-doped PdO/TiO$_2$ (PdO—Pt/TiO$_2$) pigments were synthesized. Four pigments were synthesized by adding 0.3 Wt % of Pt to PdO on TiO$_2$ in different orders and different synthetic procedures. FIG. 2 shows ΔE vs. exposure time performance for various disclosed platinum-doped PdO/TiO$_2$ pigments encapsulated in DOW 734 silicone resin that were synthesized.

All pigments with Pt dopants have an overall higher sensitivity to 100% H$_2$ gas as compared to the PK-1-135 NM1 PdO on TiO$_2$ controls (no Pt doping), except for when the Pt was first deposited on TiO$_2$ support under reflux condition (PK-1-136-NM13). However, when Pt was deposited on PdO/TiO$_2$ particles using sonication technique, a 10 fold improvement of pigment response time toward H$_2$ gas (start of visible color change, i.e. ΔE=10) was observed (sample PK-1-135-NM20). This encapsulated pigment showed a visible color change within first 10 seconds after exposure to H$_2$ gas.

Figure 3:
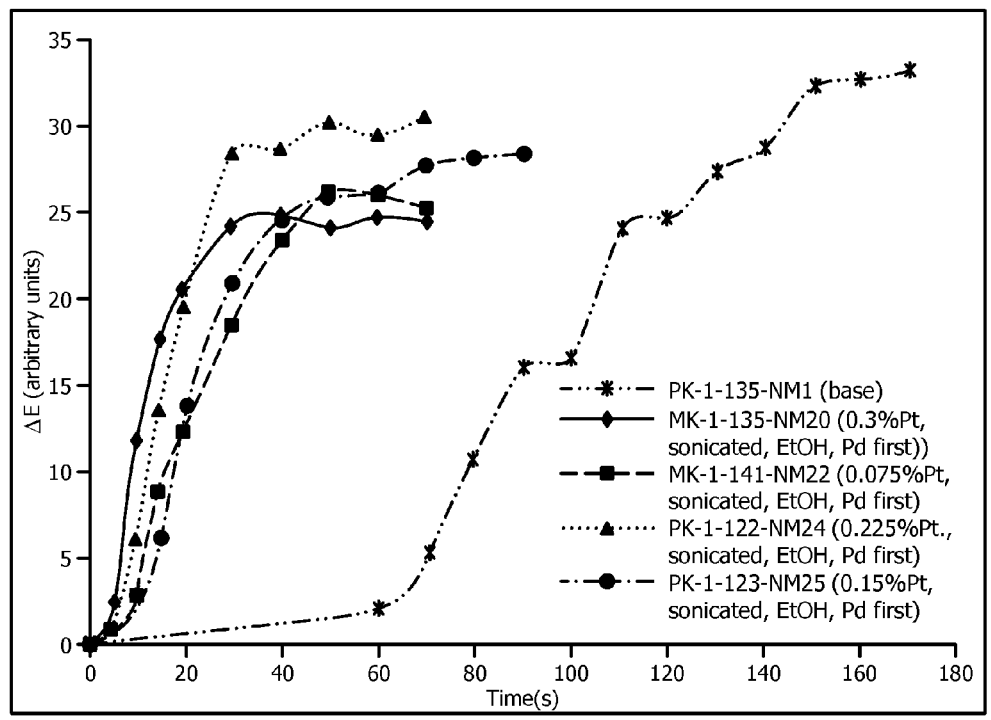
FIG. 3 shows ΔE vs. exposure time to 100% $H_2$ gas sensing performance for various disclosed platinum-doped Pd/$TiO_2$ supported oxidation catalysts used as pigments encapsulated in DOW 734® silicone resin that were synthesized having different Pt contents as compared to a known PdO on $TiO_2$ control (no Pt doping).

Furthermore, FIG. 3 shows ΔE vs. exposure time to 100% H$_2$ gas sensing performance for various disclosed platinum-doped Pd/TiO$_2$ supported oxidation catalysts used as pigments encapsulated in DOW 734® silicone resin that were synthesized having different Pt contents as compared to a known PdO on $TiO_2$ control (no Pt doping). As shown in FIG. 3, the amount of Pt can be reduced to as low as 0.075 wt. % without any significance loss in response time toward hydrogen gas compared to composite particles with 0.3 wt % of Pt dopant (see FIG. 3).

Example 5

Effect of Solvent on Platinum-Doped PdO/$TiO_2$ Pigments

Figure 4:
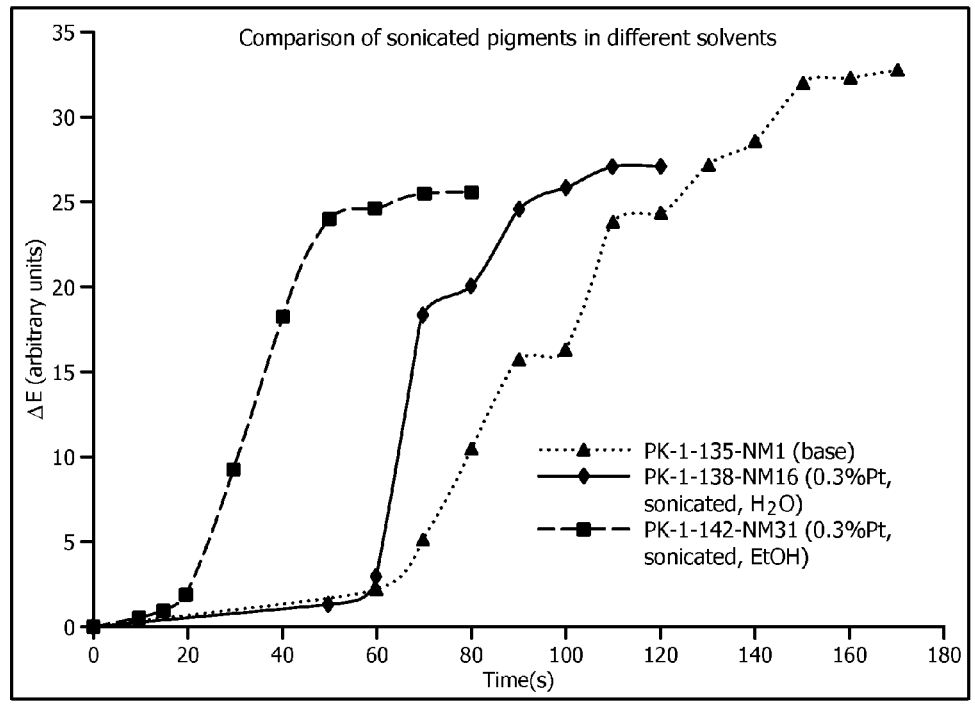
FIG. 4 shows ΔE vs. exposure time to 100% $H_2$ sensing gas for various disclosed platinum-doped $PdO/TiO_2$ supported oxidation catalysts used as pigments encapsulated in DOW 734® silicone resin that were synthesized using different solvents during sonication processing as compared to known PdO on $TiO_2$ controls (no Pt doping)

FIG. 4 shows ΔE vs. exposure time performance for a synthesized platinum-doped PdO/$TiO_2$ pigments encapsulated in DOW 734 silicone resin synthesized using water, instead of ethanol as the solvent during sonication procedure. This example showed that platinum-doped pigments synthesized in ethanol are far superior in response time toward $H_2$ compared to pigments synthesized in water (PK-1-138-NM16). When Pt was deposited using water as sonication solvent, the pigment showed no measurable improvement over non-doped PdO/$TiO_2$ pigments reflected in the PK-1-135 NM1 base/control (PdO on $TiO_2$ controls (no Pt doping).

Example 6

Exposure of PdO/$BaSO_4$ Pigments ($BaSO_4$ Supports)

Figure 5:
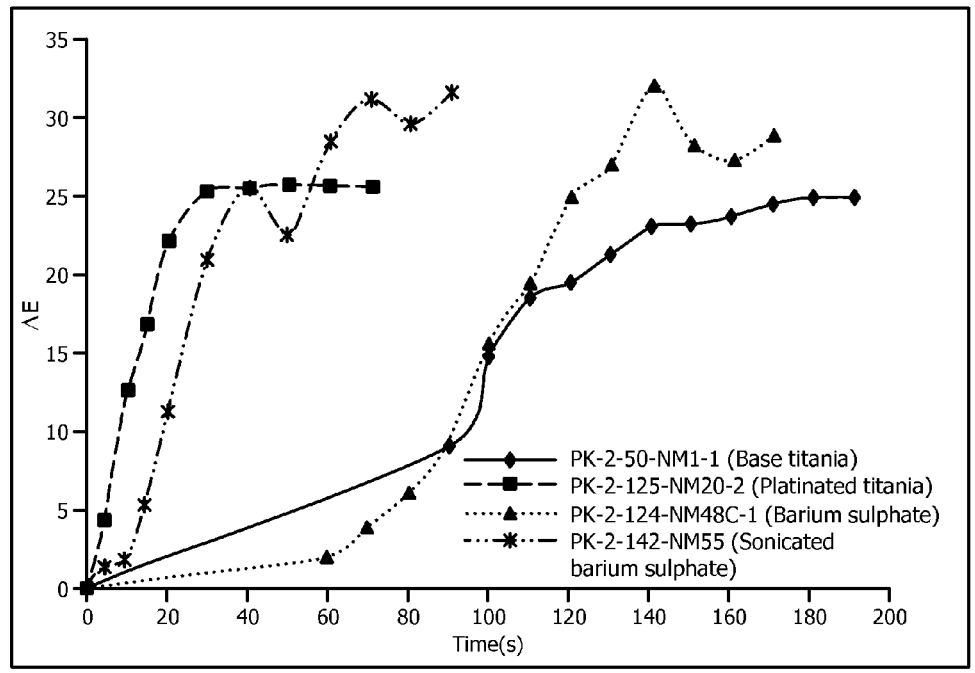
FIG. 5 shows ΔE vs. exposure time to 100% $H_2$ sensing gas for various disclosed $PdO/BaSO_4$ oxidation catalysts ($BaSO_4$ as supports) used as pigments encapsulated in DOW 734® silicone resin that were synthesized as compared to a known PdO on $TiO_2$ oxidation catalyst control (no Pt doping).

FIG. 5 shows ΔE vs. exposure time performance for two synthesized PdO/$BaSO_4$ pigments (see PK-2-124-NM48C-1 and PK-2-142-NM55 in FIG. 5) encapsulated in DOW 734 silicone resin. The PdO/$BaSO_4$ oxidation catalysts were prepared by sonication showed a response time very similar to Pt doped PdO/$TiO_2$ catalyst shown as PK-2-125-NM-20-2. This $BaSO_4$-based catalyst has eliminated the need for PMG metal dopant, and therefore will be more cost effective. However, $BaSO_4$ can be used with PMG metal dopants for even faster kinetics.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments of the invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

I claim:

1. A supported oxidation catalyst, comprising:
a support comprising a metal oxide or metal salt, and
mixed metal comprising particles on said support, including:
first particles comprising a palladium compound, and
second precious metal group (PMG) metal particles, wherein said PMG metal is not palladium.

2. The oxidation catalyst of claim 1, wherein said palladium compound comprises palladium oxide, palladium hydroxide, or a palladium salt.

3. The oxidation catalyst of claim 1, wherein said second PMG metal particles are nanosized and a relative concentration ratio of said second PMG metal particles to said first particles ranges from 1:10 to 1:25 by weight.

4. The oxidation catalyst of claim 1, wherein said PMG metal comprises gold, silver or platinum.

5. The oxidation catalyst of claim 1, further comprising an ultraviolet (UV) absorber or UV Blocker, or a mixture thereof on said support.

6. The oxidation catalyst of claim 5, wherein said UV blocker comprises zinc oxide or titania.

7. The oxidation catalyst of claim 5, wherein said UV absorber comprises a triazine family compound.

8. The oxidation catalyst of claim 1, further comprising a gas permeable polymer that provides a continuous phase that completely encapsulates said mixed metal comprising particles and said support.

9. The oxidation catalyst of claim 8, wherein said gas permeable polymer comprises silicone rubber or silicon resin.

10. The oxidation catalyst of claim 1, wherein said metal oxide or said metal salt comprise transition metal oxide particles and alkaline earth salt particles, respectively.

11. The oxidation catalyst of claim 10, wherein said transition metal oxide particles comprise Group IV metal oxide particles.

12. The oxidation catalyst of claim 11, wherein said Group IV metal oxide particles comprise at least one of TiO2, ZrO2, SrTiO3, AlTiO3 and SrZrO3.

13. The oxidation catalyst of claim 10, wherein said metal salt particles comprise alkaline earth metal salt particles.

14. The oxidation catalyst of claim 13, wherein said alkaline earth metal salt particles comprise BaSO4.

* * * * *